United States Patent [19]

Schmerling

[11] 3,959,226

[45] May 25, 1976

[54] PRODUCTION OF SUBSTITUTED AROMATIC COMPOUNDS

[75] Inventor: Louis Schmerling, Riverside, Ill.

[73] Assignee: Universal Oil Products Company, Des Plaines, Ill.

[22] Filed: Nov. 4, 1974

[21] Appl. No.: 520,697

[52] U.S. Cl. .................. 260/671 R; 260/668 R; 260/671 M; 260/671 P
[51] Int. Cl.$^2$ ........................................ C07C 3/56
[58] Field of Search ........ 260/671 R, 671 P, 671 M, 260/668 R

[56] References Cited
UNITED STATES PATENTS

| | | | |
|---|---|---|---|
| 2,477,538 | 7/1949 | Badertscher et al. | 260/671 |
| 2,486,542 | 11/1949 | Weisler et al. | 260/671 |
| 2,761,885 | 9/1956 | DeJong et al. | 260/668 |
| 2,881,226 | 4/1959 | Wadsworth | 260/671 |
| 2,897,245 | 7/1959 | Fetterly | 260/668 |
| 3,676,514 | 7/1972 | Rosenthal | 260/671 |
| 3,760,022 | 9/1973 | Schmerling | 260/671 |

*Primary Examiner*—Delbert E. Gantz
*Assistant Examiner*—C. E. Spresser
*Attorney, Agent, or Firm*—James R. Hoatson, Jr.; Raymond H. Nelson; William H. Page, II

[57] ABSTRACT

A process is disclosed for the production of substituted aromatic compounds which comprises the reaction of an aromatic hydrocarbon with a compound containing an aldehyde functional group and a saturated hydrocarbon containing a tertiary carbon atom, or which is isomerized to form a saturated hydrocarbon containing a tertiary carbon atom during the reaction, in the presence of a Friedel-Crafts catalyst.

9 Claims, No Drawings

PRODUCTION OF SUBSTITUTED AROMATIC COMPOUNDS

This invention relates to a process for the preparation of substituted aromatic compounds. More specifically, this invention relates to a process for the production of substituted aromatic compounds which comprises reacting an aromatic hydrocarbon with a compound containing an aldehyde functional group and a saturated hydrocarbon containing a tertiary carbon atom, or which isomerized to form a saturated hydrocarbon containing a tertiary carbon atom during the reaction, in the presence of a Friedel-Crafts catalyst.

The preparation of substituted aromatic compounds by the reaction of an aromatic hydrocarbon and an aldehyde is well known in the art. It is also well known in the art that the aromatic hydrocarbonaldehyde reaction may be catalyzed by the presence of a Friedel-Crafts catalyst. It has been shown by various experiments that the reaction of the aromatic hydrocarbon with the aldehyde in the presence of the Friedel-Crafts catalyst normally produces the formation of 1,1-diarylalkanes. A specific example of the state of the prior art would involve the reaction of benzene with propionaldehyde in the presence of an aluminum chloride catalyst to produce 1,1-diphenylpropane in yields of excess of 50 percent.

In contradistinction to the prior art it has now been discovered that new substituted aromatic compounds may be prepared by the reaction of an aromatic hydrocarbon with a compound containing an aldehyde functional group and a saturated hydrocarbon containing a tertiary carbon atom, or which is isomerized to form a saturated hydrocarbon containing a tertiary carbon atom during the reaction, in the presence of a Friedel-Crafts catalyst particularly aluminum chloride, aluminum bromide, zirconium chloride, or boron fluoride. The utilization of the above set forth invention will enable the manufacturer of substituted aromatic compounds a greater variety in the resultant product of the aromatic hydrocarbon-aldehyde reaction. This greater variety will result in a reduction of the cost of substituted aromatic compounds as a consequence of the greater number of charge stocks available in the preparation of the desired substituted aromatic compounds and in the decrease in reaction conditions for various substituted aromatic compounds which have been known in the art to be difficult, if not impossible, to prepare.

The desired products of the process of this invention, namely, substituted aromatic compounds, are utilized in the chemical industry in many ways. For example, n-butylbenzene may be utilized in organic synthesis, or as a medium for high boiling solvents for coating compositions in organic synthesis Isobutylbenzene may be used in organic synthesis, or as an additive to waxes; as a fixative in perfumes; in the synthesis of certain pharmaceuticals such as ephedrine; as the raw material in the preparation of other organic chemicals such as floral odors; as tear gas additives; as basic resins; etc.

It is therefore an object of this invention to provide a process for the preparation of aromatic substituted compounds.

A further object of this invention is to provide a process for the preparation of the substituted aromatic compounds utilizing a saturated hydrocarbon containing a tertiary carbon atom, or which is isomerized to form a saturated hydrocarbon containing a tertiary carbon atom during the reaction, which will permit the recovery of the desirable substituted aromatic compound.

In one aspect an embodiment of this invention resides in a process for the reaction of an aromatic hydrocarbon with a compound containing an aldehyde functional group and a saturated hydrocarbon containing a tertiary carbon atom, or which is isomerized to form a saturated hydrocarbon containing a tertiary carbon atom during the reaction, in the presence of a Friedel-Crafts catalyst at reaction conditions, and recovering the resultant substituted aromatic compound.

A specific embodiment of this invention resides in a process for the preparation of substituted aromatic compounds which comprises the reaction of benzene with propionaldehyde in the presence of methylcyclohexane at a temperature of from about 25° to about 39°C and a pressure of 1 atmosphere in the presence of an aluminum chloride catalyst and recovering the resultant substituted aromatic compounds, namely, n-propylbenzene, (methylcyclohexyl)benzene, di-n-propylbenzene and polyalkylated benzenes such as tri-n-propylbenzenes, n-propyl(methylcyclohexyl)benzenes, bis(methylcyclohexyl)bezenes and n-propylbis-(methylcyclohexyl)benzenes.

Another specific embodiment of this invention resides in a process for the preparation of substituted aromatic compounds which comprises reacting benzene with propionaldehyde in the presence of isopentane at a temperature of 95°C and a pressure of 50 atmospheres afforded by the introduction of a nitrogen gas in the presence of a catalyst comprising zirconium chloride, and recovering the resultant substituted aromatic compound, namely, isobutylbenzene, the 0-, m- and p-isomers of di-isobutylbenzene and pentylbenzenes such as 2-phenyl-3-methylbutane and t-pentylbenzene.

Other objects and embodiments will be found in the following further detailed description of the present invention.

As hereinbefore set forth the present invention is concerned with a process for the preparation of substituted aromatic compounds which comprises the reaction of an aromatic hydrocarbon with a compound containing an aldehyde functional group and a saturated hydrocarbon containing a tertiary carbon atom, or which is isomerized to form a saturated hydrocarbon containing a tertiary carbon atom during the reaction, in the presence of a Friedel-Crafts catalyst. The reaction is effected under reaction conditions which include a temperature in the range of from about 0° to about 100°C and preferably in the range of from about 10° to about 80°C. In addition, another reaction condition involves pressures, said pressures ranging from atmospheric up to about 100 atmospheres or more. When superatmospheric pressures are employed, said pressures are usually afforded by the introduction of a substantially inert gas such as nitrogen or helium into the reaction zone. The pressure may also be that of the reactants and products at the various reaction temperatures.

Another variable which may be employed in the present invention is the amount of reactants; the aromatic hydrocarbon, the compound containing the aldehyde functional group and the saturated hydrocarbon may be present in equimolar ratios or the molar ratios of any of the reactants to the other may be varied to the extent of a six-fold change from one reactant to the other.

Suitable examples of aromatic hydrocarbons which may be reacted with other suitable reactants would include all aromatic hydrocarbons within Structure I

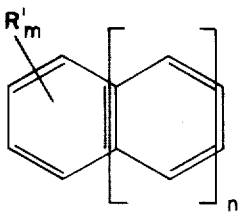

STRUCTURE I wherein n is equal to an integer of from between 0 and 5, R' is a lower alkyl possessing a carbon number range of from about 1 to about 10, cycloalkyl possessing a carbon number range of from about 3 to about 8 carbon atoms, substituted lower alkyl or substituted cycloalkyl radical and m is equal to an integer between 1 and 5. Specific examples of suitable aromatic compounds contemplated within Structure I would include benzene, anthracene, naphthalene, naphthacene, phenanthrene, chrysene, pyrene, toluene, o-xylene, m-xylene, p-xylene, ethylbenzene, cyclopentylbenzene, 1,3-dicyclohexylbenzene, etc.

Suitable examples of compounds containing an aldehyde functional group would include all aldehyde compounds within Structure II

STRUCTURE II wherein R is an alkyl radical possessing between 1 and 20 carbon atoms, aryl, cycloalkyl, alkaryl, aralkyl, alkoxy or alkylcycloalkyl radical. Specific examples of suitable aldehyde compounds would include formaldehyde, acetaldehyde, propionaldehyde, butyraldehyde, isobutyraldehyde, pentanals, heptanals, hexanals, octanals, nonanals, decananls, undecanals, dodecanals, tridecanals, tetradecanals, pentadecanals, hexadecanals, heptadecanals, octadecanals, nonadecanals, eicosanals, benzaldehyde, 2-methylbenzaldehyde, 3-methylbenzaldehyde, 4-ethylbenzaldehyde, α-naphthaldehyde, 2-butylbenzaldehyde, 4-phenylbutyraldehyde, 3,4-diphenylbutyraldehyde, 2-phenylheptanal, 3-(2,3-dimethylphenyl)octanal, cyclohexylformaldehyde, cyclopentylformaldehyde, cycloheptylformaldehyde, 2-methylcyclohexylformaldehyde, 2-ethylcyclopentylformaldehyde, 2,4-diethylcyclopentylformaldehyde, 3-methoxypropionaldehyde, 1-ethoxybutyraldehyde, 2-propoxyhexanal, etc.

Suitable examples of saturated hydrocarbons contemplated within the scope of this invention include all saturated hydrocarbons, both aliphatic and cyclic which contain tertiary carbon atoms, or which are isomerized to a saturated hydrocarbon containing such a carbon atom under the reaction conditions. These would include isobutane, isopentane, methylhexanes, methylheptanes, methyloctanes, methylnonanes, methyldecanes, and higher molecular weight branched-chain paraffins containing at least one tertiary carbon atom, and cycloalkanes containing a tertiary carbon atom such as methylcyclobutane, methylcyclopentane, methylcyclohexane, methylcycloheptane, methylcyclooctane, methylcyclononane, methylcyclodecane. Compounds which may be isomerized to hydrocarbons containing tertiary carbon atoms include n-butane, n-pentane, and cyclohexane. Suitable saturated hydrocarbons contain from about 4 to about 20 carbon atoms per molecular.

The catalysts which are utilized in the process of this invention will comprise the Friedel-Crafts catalysts including aluminum chloride, aluminum bromide, zirconium chloride and boron fluoride as a preferred catalyst. Although boron is a metalloid, for the purposes of this invention it is classified as a metal. It is also contemplated within the scope of this invention that other metallic halides such as ferric chloride, stannic chloride, titanium tetrachloride, bismuth chloride, zinc chloride as well as protonic acid catalysts such as hydrogen fluoride may be used, although not necessarily with equivalent results. It is understood that the aforementioned aromatic hydrocarbon compounds, compounds containing aldehyde functional groups, saturated hydrocarbons containing a tertiary carbon atom, or which are isomerized to form a saturated hydrocarbon containing a tertiary carbon atom during the reaction, and Friedel-Crafts catalysts are only representative of the class of compounds which may be employed, and that the present invention is not necessarily limited thereto.

The process of this invention may be affected in any suitable manner and may comprise either a batch or continuous type operation. For example, when a batch type operation is employed, the reactants comprising the aromatic hydrocarbon, the compound containing the aldehyde functional group and the saturated hydrocarbon containing a tertiary carbon atom are placed in an appropriate apparatus along with an appropriate Friedel-Crafts catalyst. If atmospheric pressure is employed, the reaction vessel is then heated to a predetermined operating temperature, often under reflux at the reflux temperature of the hydrocarbon. The reactants are maintained in the reaction vessel or autoclave at a predetermined temperature for the reaction time which may range from 0.5 up to 20 hours or more in duration, after which the heating is discontinued and the reaction or autoclave allowed to return to room temperature. The reaction mixture is then recovered, treated with water and the organic layer is separated and subjected to conventional means of purification and separation, said means including washing, drying, extraction, evaporation, fractional distillation, etc., whereby the reaction products are recovered. After recovery of the reaction products, it may be desirable to further separate and purify the various isomers of the substituted aromatic compounds. Alternatively, if superatmospheric pressures are to be employed in the reaction, the reactants and the catalysts are charged to a pressure vessel such as a rotating autoclave. The autoclave is sealed and, if desired, a substantially inert gas such as nitrogen is pressed in until the desired operating pressure is reached. The autoclave is then heated to a desired operating temperature and maintained thereat for a predetermined residence time. At the end of this predetermined residence time, the heating is terminated, the autoclave is allowed to return to room temperature and the excess pressure is discharged by a venting procedure. The autoclave is opened and the reaction mixture is then treated in a manner similar to that hereinbefore set forth whereby the desired substituted aromatic compounds and various isomers of the substituted aromatic compounds are separated and recovered.

It is contemplated within the scope of this invention that the reaction process for obtaining the substituted aromatic compounds may be effected in any continuous manner of operation. When such a type of operation is employed, the reactants comprising the aromatic hydrocarbon, the aldehyde and the saturated hydrocarbon are continuously charged to the reaction vessel containing an appropriate Friedel-Crafts catalyst, said reaction vessel being maintained at proper operating conditions of temperature and pressure. After completion of the desired residence time, the reactor effluent is continuously withdrawn and subjected to conventional means of separation whereby the desired substituted aromatic compounds and isomers of substituted aromatic compounds are recovered while any unreacted starting material comprising the aromatic hydrocarbon, aldehyde and the saturated compound are recycled to the reaction zone to form a portion of the charge stock. When the catalytic composition of matter is solid in nature (such as aluminum chloride supported on alumina, carbon or other support), various types of continuous operation may be used. One such type of operation which may be employed comprises the moving bed type operation in which the catalysts and reactants are passed through the reaction zone either concurrently or countercurrently to each other or the slurry type operation in which the catalysts is carried into the reaction zone as a slurry in either or all of the reactants.

The following examples are given to illustrate the process of the present invention and are not intended to limit the generally broad scope of the present invention in strict accordance therewith.

EXAMPLE I

In this example, a solution of 14g (0.24 moles) of propionaldehyde in 40g (0.51 moles) of benzene and 41g (0.42 moles) of methylcyclohexane was slowly added during a period of time comprising 1 hour to a stirred mixture of 40g (0.30 moles) of aluminum chloride, 20g (0.25 moles) of benzene and 81g (0.83 moles) of methylcyclohexane in a glass flask at 25°C. The temperature rose to 39°C during the addition of the solution and the methylcyclohexane. Stirring was continued for a period of time comprising 0.4 hour after which time the organic reaction product was separated from the catalyst layer, washed with water and analyzed by means of gas-liquid chromatography, infrared and mass spectroscopy.

The gas-liquid chromatography analysis segregated the various reaction products into percentages by peak areas. The peaks numbered A and 1 through 9 were found to be in the following percentages:

| Peak | Area Percent |
|------|--------------|
| A | 26% |
| 1 | 4% |
| 2 | 4% |
| 3 | 14% |
| 4 | 39% |
| 5 | 1% |
| 6 | 8% |
| 7 | 3% |
| 8 | 5% |

-continued

| Peak | Area Percent |
|------|--------------|
| 9 | 5% |

Peak A was further analyzed by infrared and mass spectroscopy and found to be n-propylbenzene. Peaks 1 to 2 were submitted to infrared and mass spectroscopy instrumentation and found to be a mixture of o-, m- and p-di-n-propylbenzene. Peaks 3 and 4 (a total of 53% of the product) were also analyzed by infrared and mass spectroscopy, said analyses disclosing the product to be various (methylcyclohexyl)benzenes. Peak 5, analyzed by infrared spectroscopy, showed an absorbent band at 700 and 755 cm$^{-1}$. Mass spectroscopy analysis indicated a molecular weight of 216.00 atomic mass units and therefore, taking both analyses in their proper perspective the conclusion reached is that the peak represented o-substituted n-propyl(methylcyclohexyl)benzene. Peak 6 was analyzed by infrared spectroscopy and found to have an absorbent band at 705 and 780 cm$^{-1}$ which suggested the m-isomer of Peak 5 or m-n-propyl(methylcyclohexyl)benzene. Peak 7 was analyzed in a similar manner and found to be the p-isomer of peaks 5 and 6 or p-n-propyl(methylcyclohexyl)benzene. Peaks 8 and 9 (each comprising 5% of the product) were analyzed by infrared spectroscopy and mass spectroscopy and found to be isomers of bis(methylcyclohexyl)benzene. The applicable percentages were determined as follows:

| Peak | Area Percent | Compound |
|------|--------------|----------|
| A | 26% | n-propylbenzene |
| 1 | 4% | Isomers of di-n-propylbenzene |
| 2 | 4% | Isomers of di-n-propylbenzene |
| 3 | 14% | Isomers of (methylcyclohexyl)benzene |
| 4 | 39% | Isomers of (methylcyclohexyl)benzene |
| 5 | 1% | o-n-Propyl(methylcyclohexyl)benzene |
| 6 | 8% | m-n-Propyl(methylcyclohexyl)benzene |
| 7 | 3% | p-n-Propyl(methylcyclohexyl)benzene |
| 8 | 5% | Isomers of bis(methylcyclohexyl)benzene |
| 9 | 5% | Isomers of bis(methylcyclohexyl)benzene |

It can be seen from the above chart that the analyses disclosed the presence of n-propylbenzene, (methylcyclohexyl)benzene, di-n-propylbenzene, and polyalkylated benzene, namely, tri-n-propylbenzenes, n-propyl(methylcyclohexyl)benzenes, bis(methylcyclohexyl)benzenes and n-propyl-bis-(methylcyclohexyl)benzenes. No diphenylpropane, the product obtained in at least 50% yield by the reaction of propionaldehyde with benzene in the presence of aluminum chloride without the presence of the saturated hydrocarbon, was observed. The products of this example are clearly a novel and unexpected result.

EXAMPLE II

In this example 78g of benzene and 36g of isopentane and 20g of zirconium chloride are placed in a 500ml three-necked glass flask equipped with a mercury-sealed stirrer, a condenser and a dropping funnel. The flask is maintained at a temperature of 40°C and a solution of 20g of isobutyraldehyde in 80g of benzene and 72g of isopentane is added to the stirred mixture during a period of time comprising 2 hours. After an additional hour of stirring at 40°C, the stirring is stopped, the mixture is cooled and the organic liquid is decanted from the catalyst, washed with water and then analyzed by means of gas-liquid chromatography, infrared and mass spectroscopy instrumentation, said analyses disclosing the product to comprise isobutylbenzene, o-, m-, and p-isomers of di-isobutylbenzene, and pentylbenzenes (chiefly 2-phenyl-3-methylbutane and t-pentylbenzene).

EXAMPLE III

In this example 10g of paraformaldehyde, 75g of benzene, and 75g of methylcyclopentane in a glass liner are sealed into an 850ml rotating autoclave; 15g of boron fluoride are pressed in together with 30 atmospheres of nitrogen. The autoclave is maintained at a temperature of 50°C for a period of time comprising 4 hours. The heating is terminated thereby allowing the autoclave to return to room temperature. The gaseous pressure is discharged and the reaction product is separated from the catalyst and analyzed by means of gas-liquid chromatography, infrared and mass spectroscopy instrumentation, said analyses disclosing the product to comprise toluene, the xylenes, isomers of (methylcyclopentyl)benzene and of (methylcyclopentyl)toluene.

EXAMPLE IV

In this example, 20g of aluminum chloride, 100g of toluene, and 70g of methylcyclopentane are weighed into a glass flask. A solution of 30g of benzaldehyde in 70g of methylcyclopentane and 50g of benzene is gradually added during a period of time comprising 2 hours; however, stirring is continued for an additional hour. At the end of this period of time, the reaction product is separated from the catalyst and analyzed by means of gas-liquid chromatography, infrared and mass spectroscopy instrumentation, said analyses disclosing the product to comprise isomers of benzyltoluene, of dibenzyltoluene and of (methylcyclopentyl)toluene.

I claim as my invention:

1. A process for the reaction of an aromatic hydrocarbon with a compound containing an aldehyde functional group and a saturated hydrocarbon containing a tertiary carbon atom, or which is isomerized to form a saturated hydrocarbon containing a tertiary carbon atom during reaction conditions, in the presence of a Friedel-Crafts catalyst without extraneous hydrogen chloride, and recovering the resultant hydrocarbyl-substituted aromatic compound.

2. The process of claim 1 further characterized in that the reaction conditions include a temperature in the range of from about 0° to about 100°C and a pressure in the range of from about 1 atmosphere to about 100 atmospheres.

3. The process of claim 1 further characterized in that said Friedel-Crafts catalyst is aluminum chloride.

4. The process of claim 1 further characterized in that said Friedel-Crafts catalyst is zirconium chloride.

5. The process of claim 1 further characterized in that said Friedel-Crafts catalyst is boron fluoride.

6. The process of claim 1 further characterized in that the aromatic hydrocarbon is benzene, the compound containing the aldehyde functional group is propionaldehyde, the saturated hydrocarbon containing a tertiary carbon atom is methylcyclohexane, and the resultant substituted aromatic compounds comprise n-propylbenzene, isomers of di-n-propylbenzene and isomers of (methylcyclohexyl)benzene.

7. The process of claim 1 further characterized in that the aromatic hydrocarbon is benzene, the compound containing the aldehyde functional group is isobutyraldehyde, the saturated hydrocarbon containing a tertiary carbon atom is isopentane and the resultant substituted aromatic compounds comprise isobutylbenzene, isomers of di-isobutylbenzene and isomers of pentylbenzene.

8. The process of claim 1 further characterized in that the aromatic hydrocarbon is benzene, the compound containing the aldehyde functional group is paraformaldehyde, the saturated hydrocarbon containing a tertiary carbon atom is methylcyclopentane and the resultant substituted aromatic compounds comprise toluene, the isomeric xylenes, and isomers of (methylcyclopentyl)benzene and of (methylcyclopentyl)toluene.

9. The process of claim 1 further characterized in that the aromatic hydrocarbon is toluene, the compound containing the aldehyde functional group is benzaldehyde, the saturated hydrocarbon containing a tertiary carbon atom is methylcyclopentane and the resultant substituted aromatic compounds comprise isomers of benzyltoluene, dibenzyltoluene and (methylcyclopentyl)toluene.

* * * * *